(12) United States Patent
Badve et al.

(10) Patent No.: US 10,247,732 B2
(45) Date of Patent: Apr. 2, 2019

(54) MATERIALS AND METHODS FOR DIAGNOSING AND PREDICTING THE COURSE OF PROSTATE CANCER

(71) Applicant: Indiana University Research and Technology Corporation, Indianapolis, IN (US)

(72) Inventors: Sunil Badve, Indianapolis, IN (US); Harikrishna Nakshatri, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 75 days.

(21) Appl. No.: 15/271,988

(22) Filed: Sep. 21, 2016

(65) Prior Publication Data

US 2017/0030916 A1 Feb. 2, 2017

Related U.S. Application Data

(63) Continuation of application No. 13/700,777, filed as application No. PCT/US2011/038823 on Jun. 1, 2011, now abandoned.

(60) Provisional application No. 61/350,339, filed on Jun. 1, 2010.

(51) Int. Cl.
*G01N 33/574* (2006.01)
*C12Q 1/6886* (2018.01)
*G01N 33/68* (2006.01)

(52) U.S. Cl.
CPC ..... *G01N 33/57434* (2013.01); *C12Q 1/6886* (2013.01); *G01N 33/6893* (2013.01); *C12Q 2600/118* (2013.01); *C12Q 2600/136* (2013.01); *C12Q 2600/158* (2013.01); *G01N 2333/4703* (2013.01); *G01N 2500/10* (2013.01); *G01N 2800/50* (2013.01)

(58) Field of Classification Search
None
See application file for complete search history.

(56) References Cited

U.S. PATENT DOCUMENTS

| 2010/0068717 A1 | 3/2010 | Badve et al. |
| 2010/0227317 A1 | 9/2010 | Thompson Okatsu et al. |
| 2011/0236903 A1 | 9/2011 | McClelland et al. |

FOREIGN PATENT DOCUMENTS

| EP | 200543 A2 | 12/2008 |
| WO | 2010065940 A1 | 10/2010 |

OTHER PUBLICATIONS

Berthold et al J Clin Oncol, 26:242-245, 2008.*
Petrylak et al, NEJM, 351:1513-1520, 2004.*
Jain, R. K. et al. High-level expression of forkhead-box protein A1 in metastatic prostate cancer. Histopathology Apr. 2011, vol. 58, No. 5, pp. 766-772.
Mirosevich, J. et al. Expression and role of Foxa proteins in prostate cancer. Prostate Jul. 1, 2006, vol. 66, No. 1 0, pp. 1013-1028.
Jain, et al., Laboratory Invest, Feb. 2010, vol. 90, Suppl 1, pp. 197A-198A.
Yu, et al., Clinical Cancer research, 2009, vol. 15, pp. 7421-7428.
Hahn, et al, Ann Oncol, 2009, vol. 20, pp. 1971-1976.
Van Der Heul-Nieuwenhuijsen, L. et al., Gene expression of forkhead transcription factors in the normal and diseased human prostate. British Journal of Urology International. Jun. 2009, vol. 103, No. 11, pp. 1574-1580.

\* cited by examiner

*Primary Examiner* — Mark Halvorson
(74) *Attorney, Agent, or Firm* — Faegre Baker Daniels LLP

(57) ABSTRACT

Expression of Forkhead-box protein A1 (FOXA1), a transcription factor important for the normal development of the prostate gland is thought to be controlled by steroid hormones and GATA-3. Expression of FOXA1, GATA-3 and androgen receptor (AR) was retrospectively analyzed by immunohistochemistry (IHC) in a series of 80 primary tumors and 28 metastatic prostate cancers including 15 matched paired samples. High nuclear FOXA1 expression was seen in 19% of primary tumors and 89% of metastatic tumors (p<0.0001). FOXA1 expression correlated positively with tumor size, extra-prostatic extension, angiolymphatic invasion, AR and metastasis but did not correlate with age, tumor stage, Gleason score, presence of PIN or multifocality, seminal vesicle or perineural invasion and status of surgical excision margins. Expression of GATA-3 was not seen in either normal epithelium or tumor. High FOXA1 expression is associated with development of metastatic prostate cancer. Accordingly, FOXA1 expression can be used to classify patients at higher risk for metastases.

11 Claims, 12 Drawing Sheets
Specification includes a Sequence Listing.

MATERIALS AND METHODS FOR DIAGNOSING AND PREDICTING THE COURSE OF PROSTATE CANCER

PRIORITY CLAIM

This application is a continuation application of U.S. patent application Ser. No. 13/700,777 (U.S. Publication No. 2013/0202717) filed on Nov. 29, 2012, which claims the benefit of PCT/US2011/038823 filed on Jun. 1, 2011, and U.S. Provisional patent application Ser. No. 61/350,339 filed on Jun. 1, 2010, all of which are hereby incorporated by reference herein in their entireties.

FIELD OF THE INVENTION

Aspects of the invention relate to diagnosing forms of metastatic prostate cancer by assaying for the expression of Forkhead-Box Protein A1 (FOXA1).

BACKGROUND

A majority of prostate cancer patients have localized disease at the time of diagnosis with the disease being confined to the gland and surrounding soft tissue. However, a small percentage of patients (about 10%) develop metastases leading to death over time. Gopalkrishnan, R. V., Kang, D. C., Fisher, P. B., Molecular markers and determinants of prostate cancer metastasis, J Cell Physiol 2001; 189; 245-256; Isaacs, J. T., Molecular markers for prostate cancer metastasis, Developing diagnostic methods for predicting the aggressiveness of prostate cancer, Am J Pathol 1997; 150; 1511-1521. In most cases micrometastases go undetected and later develop into life threatening tumors. Gopalkrishnan, et al. It is of vital importance to determine markers that could predict metastatic potential of prostate cancer in order to initiate early aggressive therapy for such tumors. Developing diagnostic methods for predicting the aggressiveness of prostate cancer, Am J Pathol 1997; 150; 1511-1521. To date, there are no commercially available reliable and accurate markers that can predict such aggressive phenotypes. Accordingly, there is a need for developing a method of identifying lesions in forms of prostate cancer. Some aspects of invention address this need.

SUMMARY

Forkhead box protein A1 (FOXA1) is a transcription factor that is important for normal development of the prostate gland. As discussed herein, FOXA1 is marker of poor prognosis that is associated with development of metastasis.

Expression of FOXA1 was analyzed by immunohistochemistry (IHC) in a series of 117 prostate cancers patients selected from the period of 2000 to 2003. Ten tissue microarrays (TMAs) were prepared using 0.6μ triplicate cores from these patients along with one core from corresponding normal tissue adjacent to the tumor foci. All TMAs were stained for FOXA1 using previously described methods and the nuclear expression was noted in primary tumor as well as in normal prostatic tissues using the Histoscore method. Statistical methods used for analyses included Spearman's correlation, Chi-square, and Fisher's exact tests.

High FOXA1 expression in primary prostate tumors correlated positively with positive metastatic status that included cases with nodal and/or distant metastases at surgery or metachronously after surgery ($p=0.006$). It also positively correlated with extra-prostatic extension ($p=0.037$), seminal vesicle invasion ($p=0.048$), perineural invasion ($p=0.008$) and T stage ($p=0.023$). It did not correlate with age, PSA level at diagnosis, Gleason score and angiolymphatic invasion.

High FOXA1 expression is related to the development of metastasis. A validation study illustrated that FOXA1 expression could be used to identify cancers with a propensity to metastasize fulfilling an unmet need for a predictor of biologic behaviour of prostate cancer. In addition, modulating FOXA1 expression in prostate cancer may be a potential therapeutic approach. Some aspects of the invention include methods of diagnosing a patient with metastatic prostate cancer or a patient having an increased risk for developing metastatic prostate cancer comprising the steps of obtaining a sample from a patient and measuring the level of FOXA1 in the sample. In some embodiments, the level of FOXA1 is measured by contacting the sample with anti-FOXA1 antibody and measuring the amount of antibody bound to FOXA1 in the sample. In some embodiments, the amount of FOXA1 measured in a given sample is compared to a collection of FOXA1 levels measured in patients with either low or high risks for developing metastatic prostate cancer. As discussed herein, patients having tumors with high levels or FOXA1 are characterized as being at higher risk for developing metastatic prostate cancer than patient having lower levels of FOXA1.

Some aspects of the invention include methods of diagnosing prostate cancer, comprising the steps such as contacting a sample from a patient with a first reagent, wherein the first reagent selectively interacts with at least a portion of an expression product of the FOXA1 gene and wherein the interaction produces a detectable signal; determining the level of the transcription factor FOXA1 in the sample by measuring the detectable signal produced by the interaction between the first reagent and the gene product, and correlating the measured signal with the likelihood that the patient's prostate cancer will metastasize, wherein a low level FOXA1 expression indicates a lessened risk for metastasis; and wherein a high level of FOXA1 expression indicates a greater risk for metastasis. In some embodiments, the sample includes cancer cells from a patient's prostate.

In some embodiments, the signal associated with the presence of FOXA1 expression product such as RNA or a polypeptide can be detected directly, by using, for example, a polypeptide that hybridizes to a portion of RNA and includes a radioactive, fluorogenic or visible moiety. In some embodiments, the signal is associated with a reagent such as an antibody that binds to a portion of the polypeptide encoded by the FOXA1 gene. In some embodiments, the antibody is labelled with a radioactive, fluorogenic, chemiluninescent, or visible moiety. In some embodiments, the signal is produced by a second reagent that binds to the first reagent. For example, in some embodiments, the first reagent may be an antibody that binds to a portion of the FOXA1 transcription factor and second labelled reagent may be a second antibody that binds to the first antibody. In some embodiment, antibody is goat anti-human FOXA1 antibody.

In some embodiments, the level of FOXA1 expression is determined by scoring the sample, in a method that includes the steps of: recording the intensity (I) of the signal produced by the sample after contacting the sample with the first reagent; observing the percentage (P) of cells in the sample that produce a signal; and determining the score of the sample by multiplying the recorded intensity (I) by the observed percentage (P) of cells. In some embodiments, the intensity of the signal is graded according to the following scale: none (0); mild (+1); moderate (+2); and strong (+3). And, in some embodiments, the percentage of the cells that react with the reagent to produce a signal ranges from 0 to 100.

In some embodiments, the intensity is graded according to the following scale: none (0); mild (+1); moderate (+2); and strong (+3) and the percentage ranges from 0 to 100 and the signal ranges from 0 to 300. In some embodiments that use this form of scoring the value of the level of FOXA1 expression product greater than about 275 is indicative of a form of prostate cancer with a high likelihood of metastasizing. In other embodiments that use this form of scoring, FOXA1 expression product greater than about 280 is indicative of a form of prostate cancer with a high likelihood of metastasizing. While in still other embodiments that use this form of scoring, a sample with a level of FOXA1 expression product less than about 150 is indicative of a form of prostate cancer with low likelihood of metastasizing.

Some aspects of the invention include methods of screening for a compound to treat prostate cancer, comprising the steps of: providing a prostate cancer cell that expresses high level of the transcription factor FOXA1; contacting said prostate cancer cell with at least one compound; and measuring the viability of prostate cells after contacting said cells with the compound. Some embodiments of screening for compounds that can effectively treat or to some extent prevent metastatic prostate cancer include the step of identifying compounds that selectively reduce the viability of prostate cancer cells that highly express FOXA1 without affecting non-cancerous prostate cancer cells.

Still other embodiments of the invention include methods for treating prostate cancer, especially forms of prostate cancer that have a propensity to metastasize. Some of these methods comprise the steps of: providing at least one compound or a pharmaceutically acceptable salt thereof that modulates the activity FOXA1 or an expression product of FOXA1. Still other embodiments include treating a patient with the compound or a pharmaceutically acceptable salt thereof. In some embodiments, the compounds may interfere with the expression of the FOXA1 gene either by preventing its translation or by interfering with its transcription. In still other embodiments, the compound may alter the activity of polypeptide encoded by the FOXA1 gene either by binding to the protein itself or by interacting with the protein's target binding site.

SEQUENCE LISTING

Figure 1A:
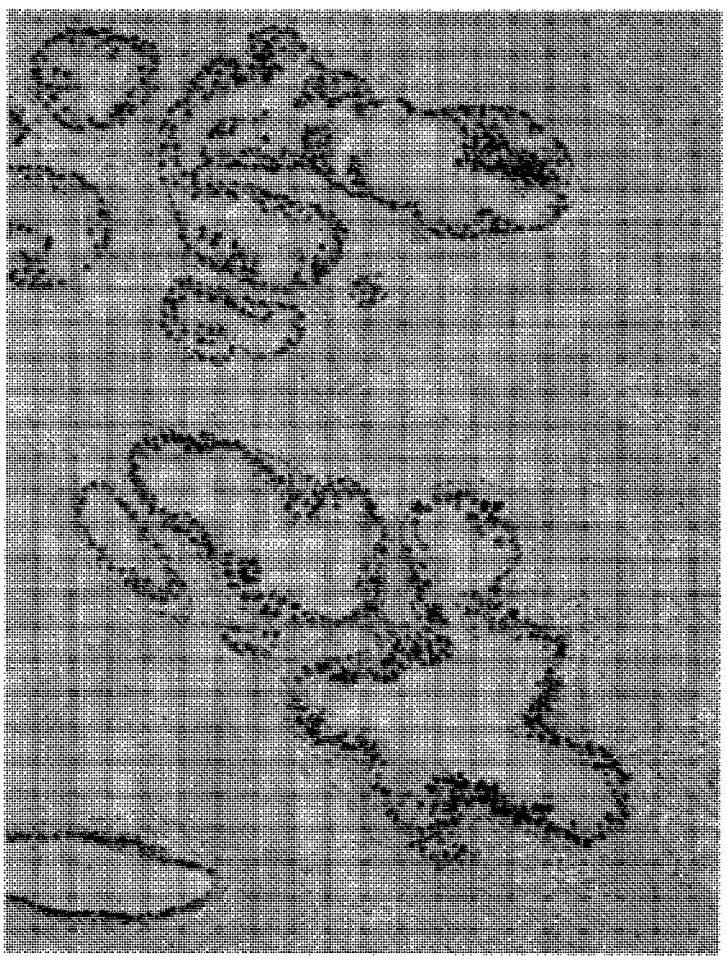
FIG. 1A. Photomicrograph showing expression of FOXA1 in luminal cells in normal glands.
Figure 1B:
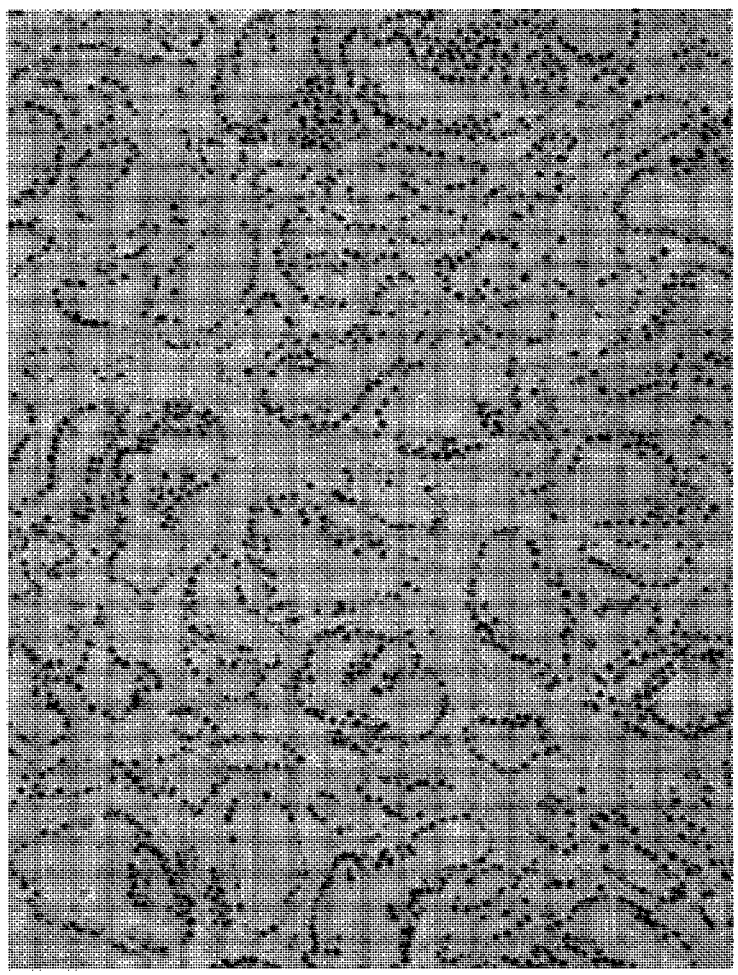
FIG. 1B. Photomicrograph showing varying degrees of FOXA1 expression in Gleason patterns.
Figure 1C:
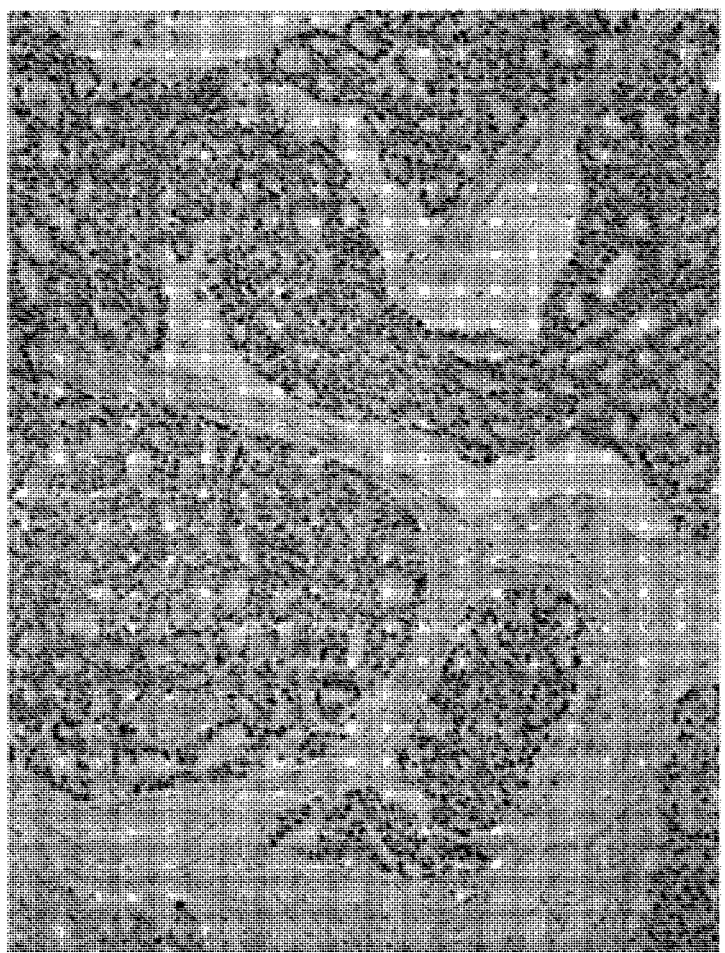
FIG. 1C. Photomicrograph showing varying degrees of FOXA1 expression in Gleason patterns.
Figure 1D:
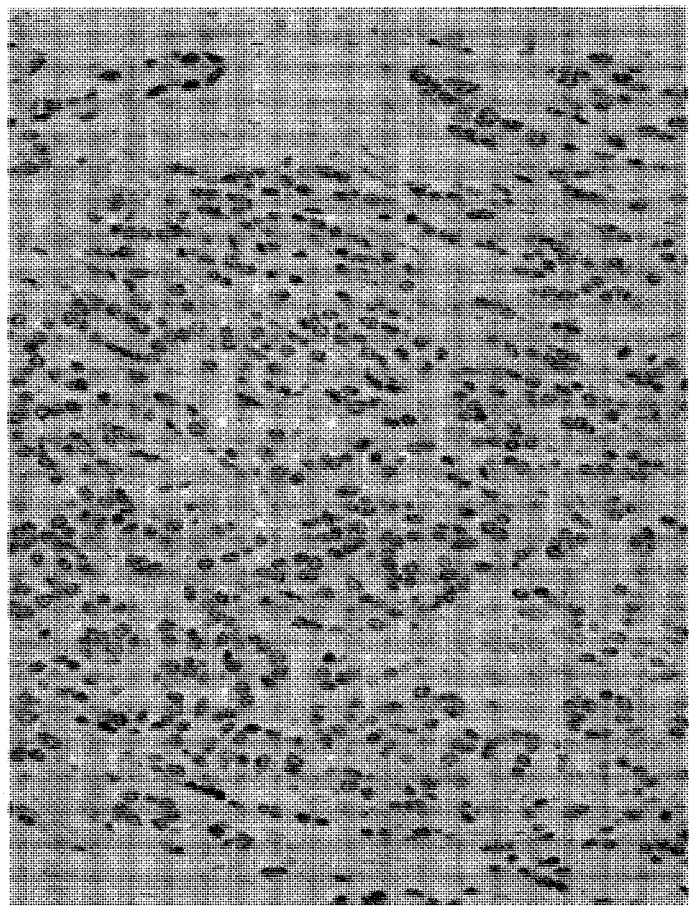
FIG. 1D. Photomicrograph showing varying degrees of FOXA1 expression in Gleason patterns.
Figure 2A:
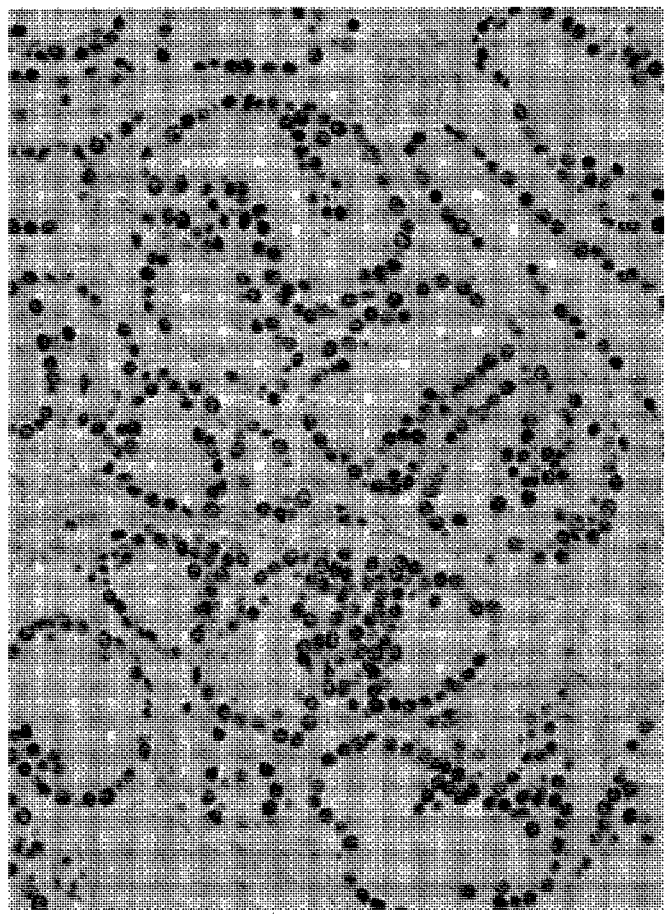
FIG. 2A. Photomicrograph showing high expression of FOXA1 in primary prostate cancer tumor.
Figure 2B:
FIG. 2B. Photomicrograph showing high expression of FOXA1 in synchronous lymph node metastasis.
Figure 2C:
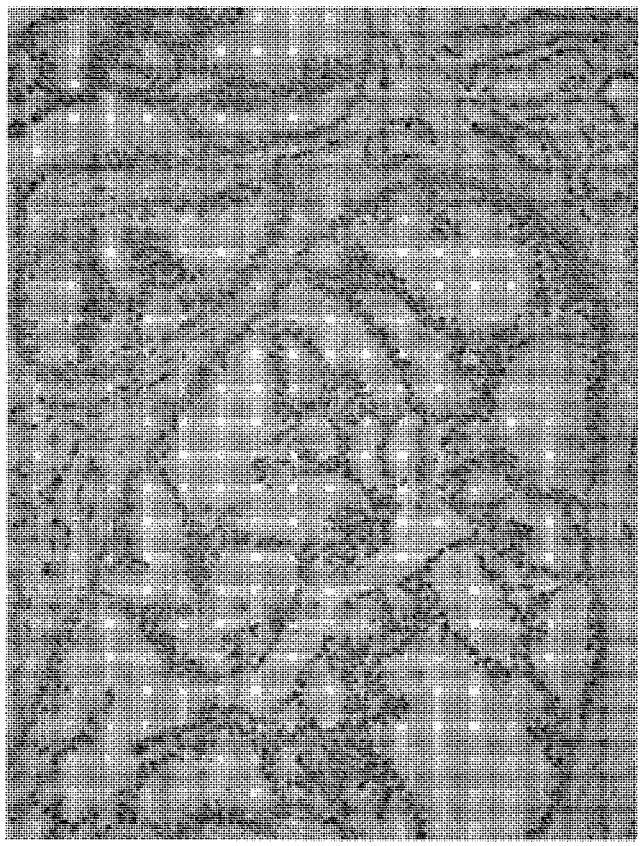
FIG. 2C. Photomicrograph showing high expression of FOXA1 in synchronous primary tumor.
Figure 2D:
FIG. 2D. Photomicrograph showing high expression of FOXA1 metachronic distant metastasis.

SEQ ID NO. 1 FOXA1 polynucleotide sequence from Homo sapiens.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of the claimed invention.

The role of androgen as well as androgen receptor in cancer cell growth and development has been described. The compounds are implicated not only in the normal growth, differentiation and maintenance of the prostate gland but are also important mediators of prostate cancer development. Li, R., Wheeler, T., Dai, H., Frolov, A., Thompson, T., Ayala, G., High level of androgen receptor is associated with aggressive clinicopathologic features and decreased biochemical recurrence-free survival in prostate: cancer patients treated with radical prostatectomy, *Am J Surg Pathol* 2004; 28; 928-934. Alterations in androgen receptor activity through signal transductions, mutations and expression of its coregulators are some of the pathways suggested in the progression of prostate cancer. Heinlein, C. A., Chang, C., Androgen receptor in prostate cancer, *Endocr Rev* 2004; 25; 276-308. Due to the intricate role of androgen in prostate cancer, androgen deprivation therapy in the form of pharmacologic preparations or castration is widely instituted in metastatic prostate cases. Mellado, B., Codony, J., Ribal, M. J., Visa, L., Gascon, P., Molecular biology of androgen-independent prostate cancer: the role of the androgen receptor pathway, *Clin Transl Oncol* 2009; 11; 5-10.

Androgens and their receptors (AR) are essential for the development and maintenance of normal prostate. Li, R., et al. Am J Surg Pathol 2004; 28; 928-934; Hobisch, A., Culig, Z., Radmayr, C., Bartsch, G., Klocker, H., Hittmair, A., Androgen receptor status of lymph node metastases from prostate cancer, *Prostate* 1996; 28; 129-135. Aberrations in this signal transduction system result in tumor progression and androgen independence. Heinlein, C. A., et al., *Endocr Rev* 2004; 25; 276-308. AR expression has been noted in prostate carcinoma including tumors resistant to endocrine therapy. Hobisch, A., et al., *Prostate* 1996; 28; 129-135. Compared to benign prostate, a greater heterogeneity and decreased intensity of AR expression has been reported in prostate cancer. Li, R., et al., *Am J Surg Pathol* 2004; 28; 928-934; Miyamoto, K. K., McSherry, S. A., Dent, G. A., et al, Immunohistochemistry of the androgen receptor in human benign and malignant prostate tissue, *J Urol* 1993; 149; 1015-1019. However, similar to Cardillo, et al., as reported herein, an increase in AR expression in primary prostate cancer was observed. Cardillo, M. R., Petrangeli, E., Salvatori, L., Ravenna, L., Di Silverio, F., Transforming growth factor beta 1 and androgen receptors in prostate neoplasia, *Anal Quant Cytol Histol* 2000; 22; 403-410. A significant difference in AR expression in primary and metastatic lesions was not found; these findings are similar to those reported by Hobisch, et al. Hobisch, A., Culig, Z., Radmayr, C., Bartsch, G., Klocker, H., Hittmair, A., Androgen receptor status of lymph node metastases from prostate cancer, *Prostate* 1996; 28; 129-135; 23; Dunsmuir, W. D., Gillett, C. E., Meyer, L. C., et al., Molecular markers for predicting prostate cancer stage and survival, *BJU Int* 2000; 86; 869-878. In contrast, Li, R., et al., have observed a decreased expression of AR at all metastatic sites. Li, R., et al., *Am J Surg Pathol* 2004; 28; 928-934. Li, R., et al., also found an association of AR with Gleason grade/score. However, this was not reported by Dunsmuir, et al., Dunsmuir, W. D., Gillett, C. E., Meyer, L. C., et al., Molecular markers for predicting prostate cancer stage and survival, *BJU Int* 2000; 86; 869-878, or observed in the current study.

The role of GATA-3 in normal prostate development and function as well as pathogenesis of prostate cancer is poorly understood. In mice and in human studies, high GATA-3 mRNA expression has been noted in both embryonic and adult prostatic tissues. Perez-Stable, C. M., Pozas, A., Roos, B. A. A role for GATA transcription factors in the androgen regulation of the prostate-specific antigen gene enhancer, *Mol Cell Endocrinol* 2000; 167; 43-53. Its expression in prostate cancer cell lines is reported to be very low. Perez-Stable, C. M., et al., *Mol Cell Endocrinol* 2000; 167; 43-53. This could explain why this study failed to observe GATA-3 expression in normal, primary or metastatic prostate tissues by immuno-histochemistry.

FOXA1 transcription factor plays an important role in the development of prostate gland and has been implicated in prostate cancer. After its first identification in the liver, Nakshatri, H., Badve, S., FOXA1 as a therapeutic target for breast cancer, *Expert Opin Ther Targets* 2007; 11; 507-514, FOXA1 expression has also been observed in colon, lung, thyroid and esophageal cancers. Lin, L., Miller, C. T., Contreras, J. I., et al., The hepatocyte nuclear factor 3 alpha gene, HNF3alpha (FOXA1), on chromosome band 14q13 is amplified and overexpressed in esophageal and lung adenocarcinomas, *Cancer Res* 2002; 62; 5273-5279; Nucera, C., Eeckhoute, J., Finn, S., et al., FOXA1 is a potential oncogene in anaplastic thyroid carcinoma, *Clin Cancer Res* 2009; 15; 3680-3689. FOXA1 is also necessary for estrogen signaling in breast cancer cells and has been associated with good prognosis. Badve, S., Turbin, D., Thorat, M. A., et al., FOXA1 expression in breast cancer correlation with luminal subtype A and survival, *Clin Cancer Res* 2007; 13; 4415-4421; Thorat, M. A., Marchio, C., Morimiya, A., et al., Forkhead box A1 expression in breast cancer is associated with luminal subtype and good prognosis, *J Clin Pathol* 2008; 61; 327-332. For additional information on this gene and its role in the treatment and diagnosis of breast cancer, please see U.S. patent publication number US 2010/00687171 A1 published on Mar. 18, 2010 and incorporated herein by reference in its entity. FOXA1 has been suggested to influence AR binding to chromatin in both androgen-dependent and androgen-independent prostate cancers. Lupien, M., Eeckhoute, J., Meyer, C. A., et al., FoxA1 translates epigenetic signatures into enhancer-driven lineage-specific transcription, *Cell* 2008; 132; 958-970; Wang, Q., Li, W., Zhang, Y., et al., Androgen receptor regulates a distinct transcription program in androgen independent prostate cancer, *Cell* 2009; 138; 245-256. Epithelial FOXA1 expression has been noted in all stages of development and differentiation of the prostate. Gao, N., Zhang, J., Rao, M. A., et al., The role of hepatocyte nuclear factor-3 alpha (Forkhead Box A1) and androgen receptor in transcriptional regulation of prostatic genes, *Mol Endocrinol* 2003; 17; 1484-1507; Mirosevich, J., Gao, N., Matusik, R. J., Expression of Foxa transcription factors in the developing and adult murine prostate, *Prostate* 2005; 62; 339-352. Its expression has been observed in malignant prostatic adenocarcinoma; however its precise role is unknown. Mirosevich, J., Gao, N., Gupta, A., Shappell, S. B., Jove, R., Matusik, R. J., Expression and role of Foxa proteins in prostate cancer, *Prostate* 2006; 66; 1013-1028.

ER, FOXA1 and GATA-3 form an important transcription factor network necessary for the normal development of luminal breast epithelium. Badve, S., et al., *Clin Cancer Res* 2007; 13; 4415-4421; Eeckhoute, J., Keeton, E. K., Lupien, M., Krum, S. A., Carroll, J. S., Brown, M., Positive cross-regulatory loop ties GATA-3 to estrogen receptor alpha expression in breast cancer, *Cancer Res* 2007; 67; 6477-6483. More importantly, GATA-3 expression is believed to be required for the expression of FOXA1. The expression of GATA-3 has been demonstrated in the prostate where it has been shown to play a role in the androgen regulation of the prostate specific antigen (PSA) gene. Lakshmanan, G., Lieuw, K. H., Lim, K. C., et al., Localization of distant urogenital system-, central nervous system-, and endocardium-specific transcriptional regulatory elements in the GATA-3 locus, *Mol Cell Biol* 1999; 19; 1558-1568. However, its role in the development of prostate cancer is as yet not known. Lakshmanan, G., et al., *Mol Cell Biol* 1999; 19; 1558-1568.

As reported herein, the expression of FOXA1 and its potential role in prostate cancer was analyzed; the expression of GATA-3 and AR by immunohistochemistry to further study this transcription factor network was also analyzed. This analysis shows that there is high FOXA1 expression in patients with metastatic prostate adenocarcinomas.

FOXA1 has been recognized as an important transcription factor that modulates the functions of steroid hormone receptors like ER in breast or AR in prostate. Gao, N., et al., *Mol Endocrinol* 2003; 17; 1484-1507. Studies in both mice and in humans have demonstrated that FOXA1 binds to DNA at or near androgen response elements (AREs). Gao, N., et al., *Mol Endocrinol* 2003; 17; 1484-1507. This facilitates the expression of androgen regulated prostate-specific genes leading to prostate organogenesis and function. Gao, N., et al., *Mol Endocrinol* 2003; 17; 1484-1507. High FOXA1 expression has been described in mouse models at all stages of prostate development. Mirosevich, J., et al., *Prostate* 2005; 62; 339-352; Mirosevich, J., Gao, N., Gupta, A., Shappell, S. B., Jove, R., Matusik, R. J., Expression and role of Foxa proteins in prostate cancer, *Prostate* 2006; 66; 1013-1028. In these models, FOXA1 deficiency results in aberrant prostate ductal morphogenesis. Gao, N., Ishii, K., Mirosevich, J., et al., Forkhead box A1 regulates prostate ductal morphogenesis and promotes epithelial cell maturation, *Development* 2005; 132; 3431-3443. A strong expression of mouse Foxa1 by immunohistochemistry has been noted in normal prostate and in prostate cancer. Mirosevich, J., et al., *Prostate* 2005; 62; 339-352.

One recent RT-PCR based study analyzed the expression of 12 different FOX genes in normal prostate and prostatic cancer and found that FOXA1 and FOXC1 correlated with androgen associated growth status of cancer. Culig, Z., Klocker, H., Eberle, J., et al., DNA sequence of the androgen receptor in prostatic tumor cell lines and tissue specimens assessed by means of the polymerase chain reaction, *Prostate* 1993; 22; 11-22. Consistent with this, a strong positive correlation between FOXA1 and AR in primary prostate cancers was observed in the initial study. Although it has been suggested that FOXA1 represses PSA promoter activity in prostate cancer cells; Lee, H. J., Hwang, M., Chattopadhyay, S., Choi, H. S., Lee, K., Hepatocyte nuclear factor-3 alpha (HNF-3alpha) negatively regulates androgen receptor transactivation in prostate cancer cells, *Biochem Biophys Res Commun* 2008; 367; 481-486; it was not possible to demonstrate a significant correlation between serum PSA levels and FOXA1 expression in primary tumor.

In primary tumors high expression of FOXA1 was associated with poor prognostic markers such as extraprostatic extension, angiolymphatic invasion and increase in tumor size. High FOXA1 expression was also associated with higher propensity towards metastasis. Surprisingly, the expression of FOXA1 was not associated with Gleason pattern or score. This finding is similar to that reported with regards to the expression of mouse Foxa1 in prostate cancer. Mirosevich, J., et al., *Prostate* 2005; 62; 339-352; Mirosevich, J., et al., *Prostate* 2006; 66; 1013-1028. Those results suggest that FOXA1 is a marker of poor prognosis.

Another unexpected finding reported herein is the frequency of high FOXA1 expression in metastatic tumors (89%). Importantly, high expression of FOXA1 was seen in primary tumors of almost half the cases with synchronous metastases. These results demonstrate that high FOXA1 expression is causally related to the development of metastasis. Its expression is likely further increased at metastatic sites. This also raises the strong possibility that the expression of FOXA1 or its downstream molecules could be used as predictive marker in prostate cancer.

Nucleic acid or nucleic acid sequence or polynucleotide or polynucleotide sequence refers to the sequence of a single- or double-stranded DNA or RNA molecule of genomic or synthetic origin, i.e., a polymer of deoxyribonucleotide or ribonucleotide bases, respectively.

Detection of expression of FOXA1 and any other genes include detecting the expression of RNA and the resulting protein products thereof. For example, FOXA1 RNA can be detected using in situ RT-PCR or standard PCR or through any hybridization techniques that involve probes. RNA expression can also be quantified by any known quantification PCR (qPCR) and competitive PCR technology. Microarrays are also useful in quantifying FOXA1 gene expression. RNA can be extracted from a cancer tissue, converted into cDNA and quantified using any known method. RNA can also be directly quantified in situ, within the cancer tissue itself. Probes specific to FOXA1 and ERα and PR may display a high stringency hybridization. Similar techniques are also useful in determining the expression pattern and quantity of other genes such as ERα and PR in the cancer tissues.

FOXA1 protein detection can also be carried in situ or after protein extraction from cancer tissue. Antibodies including monoclonal antibodies against FOXA1 are useful in quantifying FOXA1 protein. Standard immuno histochemistry techniques are capable of detecting the presence and the amount of FOXA1 Antibodies to FOXA1 are either directed to the full length FOXA1 protein or a peptide fragment thereof. Binding specificity of the antibodies to FOXA1 and ER and PR or any other marker disclosed herein conforms to the standards used in immunohistochemistry methodology. The antibodies include monoclonal or polyclonal antibodies.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

A "predictive marker" as used herein refers to a factor that indicates sensitivity or resistance to a specific treatment. Thus, a predictive marker provides a measure of likelihood of response or resistance to a particular therapy.

As used herein under stated as clearly indicated otherwise, the term "about" is equal to a range of 10 percent, for example, about 1.0 encompasses the range of values from 0.9 to 1.1.

For example, FOXA1 expression is used as both a prognostic marker (e.g., better response in ER positive tumors) and as a predictive marker (greater likelihood of response to anti-hormonal therapy).

A "sample" (also used as "biological sample" or "tissue or cell sample") includes a variety of sample types obtained from an individual and can be used in a diagnostic or monitoring assay. The term includes blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

A "section" of a tissue sample is meant a single part or piece of a tissue sample, e.g., a thin slice of a prostate cancer tissue or cells cut from a tissue sample. In some embodiments, the same section of tissue sample is analyzed at both morphological and molecular levels, or is analyzed with respect to both protein and nucleic acid.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

The term "antibody" herein is used in the broadest sense and specifically covers intact monoclonal antibodies, polyclonal antibodies, multi-specific antibodies (e.g., bi-specific antibodies) formed from at least two intact antibodies, and antibody fragments.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

Examples of cancers include breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, lymphoma, glioma, and multi-drug resistant cancer.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below.

A "chemotherapeutic agent" is a chemical compound useful in the treatment of cancer. Specific chemotherapy for cancers include paclitaxel, docetaxel, cisplatin, methotrexate, cyclophosphamide, 5-fluoro uridine, Leucovorin, Irinotecan (CAMPTOSAR or CPT-11 or Camptothecin-11 or Campto), Paclitaxel, Carboplatin, doxorubicin, fluorouracil carboplatin, edatrexate, gemcitabine, or vinorelbine or a combination thereof.

The identification and analysis of molecular markers, especially those of FOXA1, may have numerous therapeutic and diagnostic purposes. Clinical applications include, for example, detection of disease; distinguishing disease states to determine prognosis, selection of therapy, and/or prediction of therapeutic response; disease staging; identification of disease processes; prediction of efficacy of therapy; monitoring of patients trajectories (e.g., prior to onset of disease); prediction of adverse response; monitoring of therapy associated efficacy and toxicity; prediction of probability of occurrence; recommendation for prophylactic measures; and detection of recurrence.

The molecular markers disclosed herein may be detected using any suitable conventional analytical technique including but not limited to, immunoassays, protein chips, multiplexed immunoassays, complex detection with aptamers, chromatographic separation with spectrophotometric detection, mass spectroscopy, cDNA microarrays, and nucleic acid probe hybridization.

In an embodiment, methods to determine whether a patient sample is FOXA1 positive include using cut-off analysis based on the X tile analysis (Camp, et al., 2004). For example, S-score values of 0-3 are considered as $FOXA1_k$ and 4-30 as $FOXA1_{high}$ in determining the correlation of FOXA1 expression for predicting long-term survival rates. Other range FOXA1 includes 1-10 versus 11-30. Survival difference is statistically significant with 11-30 doing better (pi).0431).

Novel methods for diagnosis and prognosis evaluation for prostate cancer, as well as methods for screening for compositions which modulate prostate cancer and compositions which bind to modulators of prostate cancer are provided. In one aspect, the expression levels of genes such as FOXA1 are determined in different patient samples for which either diagnosis or prognosis information is desired. An expression profile (either gene expression or protein expression profiles) of a particular sample is a "fingerprint" of the state of the sample and is also considered a "molecular signature" of the state of the cancer. The intensity of expression of the genes of interest along with the temporal-spatial configurations aid in the evaluation of the expression profile for prognosis. Normal tissue may be distinguished from prostate cancer tissue, and within prostate cancer tissue, different prognosis states (low or high likelihood of prostate cancer metastasizing, for example) may be determined. In some embodiments, the evaluation of a particular treatment regime may be evaluated. Similarly, diagnosis may be done or confirmed by comparing patient samples with known signatures.

Molecular signatures or expression profiles identified herein (e.g., highly expressed FOXA1) that increase the likelihood of prostate cancer metastasizing, allow screening of drug candidates capable of mimicking or altering a desirable expression profile and thereby converting a poor prognosis profile to a better prognosis profile. This may be done by obtaining prostate cancer cell lines that tend to metastasis and testing the effects of candidate drugs on the expression profiles of FOXA1. These methods can also be done on the protein level, that is, evaluating protein expression levels of the prostate cancer proteins through antibody techniques or otherwise or at a nucleic acid level by quantifying the presence of RNA transcripts either directly or through indirect amplification techniques.

FOXA1 expression or any other marker expression in the test biological sample (i.e., the biological sample from the patient having cancer or suspected of having cancer) may be compared to a suitable control sample, as is well known in the art. Exemplary controls include comparable normal samples (e.g., normal non-cancerous tissue or cells of the same type as present in the test biological sample); matched normal samples from the same patient, universal control samples, or a normal reference value (also termed a control reference value). As used herein, the term "control" or "control sample" encompasses a normal reference value. Methods for comparison of expression levels (such as presence or absence of or amount of expression) are known in the art.

As discussed herein, expression in a biological sample can be detected by a number of methods which are well known in the art, including but not limited to, immunohistochemical and/or Western analysis, biochemical enzymatic activity assays, in situ hybridization, Northern analysis and/or PCR analysis of mRNAs, and genomic Southern analysis (to examine, for example, gene deletion or amplification), as well as any one of the wide variety of assays that can be performed by gene, protein, and/or tissue array analysis.

Nucleic acid or nucleic acid sequence or polynucleic acid wide or polynucleotide sequence refers to the sequence of a single or double-stranded DNA or RNA molecule of genomic or synthetic origin, i.e., a polymer of deoxyribonucleotide or ribonucleotide bases, respectively.

Analysis of expression levels (RNA or protein or both) of FOXA1 are useful for identifying a prostate cancer patient's likelihood of developing a form of prostate cancer that will metastasize. Such analysis is also useful in prognosing metastasis of prostate cancers that have differential FOXA1 expression.

Detection of expression of FOXA1 and any other genes include detecting the expression of RNA and the resulting protein products thereof. For example, FOXA1 RNA can be detected using in situ RT-PCR or standard PCR or through any hybridization techniques that involve probes. RNA expression can also be quantified by any known quantification PCR (qPCR) and competitive PCR technology. Microarrays are also useful in quantifying FOXA1 gene expression. RNA can be extracted from a cancer tissue, converted into cDNA and quantified using any known method. RNA can also be directly quantified in situ, within the cancer tissue itself. Probes specific to FOXA1 and ERα and PR may display a high stringency hybridization. Similar techniques are also useful in determining the expression pattern and quantity of other genes such as ERα and PR in the cancer tissues.

FOXA1 protein detection can also be carried in situ or after protein extraction from cancer tissue. Antibodies including monoclonal antibodies against FOXA1 are useful in quantifying FOXA1 protein. Standard immuno histochemistry techniques are capable of detecting the presence and the amount of FOXA1 Antibodies to FOXA1 are either directed to the full length FOXA1 protein or a peptide fragment thereof. Binding specificity of the antibodies to FOXA1 and ER and PR or any other marker disclosed herein conforms to the standards used in immunohistochemistry methodology. The antibodies include monoclonal or polyclonal antibodies.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

A "predictive marker" as used herein refers to a factor that indicates sensitivity or resistance to a specific treatment and/or to the likelihood that a particular event is likely to occur will take a given predetermined course. Thus, a predictive marker provides a measure of likelihood of response or resistance to a particular therapy or to an event such prostate cancer metastasizing. For example, FOXA1 expression is used as both a prognostic marker (e.g., increased risk for metastasizing prostate cancer) and as a predictive marker (greater likelihood of metastasizing).

A "sample" (also used as "biological sample" or "tissue or cell sample") includes a variety of sample types obtained from an individual and can be used in a diagnostic or monitoring assay. The term includes blood and other liquid samples of biological origin, solid tissue samples such as a biopsy specimen or tissue cultures or cells derived there from, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

EXPERIMENTS

Materials and Methods

Sixty-five cases of primary prostate adenocarcinomas and 13 cases of metastatic prostate cancer from 2008-9 were analyzed for FOXA1 expression. Based on the initial results, additional 15 primary tumors and their synchronous metastases were also analyzed. All of the patients were treated primarily by surgery for clinically localized disease and none of them had received prior systemic therapy. Clinico-pathologic data like age, tumor size, Gleason grade, location of tumor, multifocality, extra-prostatic extension, seminal vesicle invasion, presence of high grade prostatic intraepithelial neoplasia, angio-lymphatic invasion, perineural invasion and the TNM stage were obtained through a retrospective review of medical charts. Pre-operative PSA levels, if available, were also recorded. The study was approved by the Institutional Review Board at Indiana University School of Medicine.

Following histological review, one block per case was identified for immunohistochemistry. Expression of FOXA1 and GATA3 was analyzed using goat anti-human FOXA1 antibody and goat anti-human GATA3 antibody (Santa Cruz Biotechnology) respectively using previously described methods. Badve, S., et al., *Clin Cancer Res* 2007; 13; 4415-4421; Ademuyiwa, F. O., Thorat, M. A., Jain, R. K., Nakshatri, H., Badve, S., Expression of Forkhead-box protein A1, a marker of luminal A type breast cancer, parallels low Oncotype DX 21-gene recurrence scores, *Med Pathol* 2009.

In concordance with prior literature, percentage of AR expression was recorded. Li, R., et al., *Am J Surg Pathol* 2004; 28; 928-934. Expression of FOXA1 and GATA-3 was recorded both as intensity and percentage. Percentage ranged from 0 to 100 and intensity was graded as none (0), mild (1+), moderate (2+) and strong (3+). Percentage (P) and intensity (I) of nuclear expression were multiplied to generate a numerical expression score (S=P×I) ranging from 0 to 300.

Statistical Analyses

All data were analyzed using SPSS 17.0 (SPSS, Inc., Chicago, Ill., USA). Bi-variate correlations of FOXA1, AR and GATA3 expression with each other and with age, tumor size, location of tumor, status of surgical margins, multifocality, extra-prostatic extension, seminal vesicle invasion, presence of high grade prostatic intraepithelial neoplasia, angio-lymphatic invasion, perineural invasion, TNM stage and pre-operative PSA levels were analyzed using Spearman correlation test. Gleason grade was analyzed both as individual pattern as well as combined score (high grade (>6) and low grade (≤6)). Kallakury, B. V., Sheehan, C. E., Ambros, R. A., Fisher, H. A., Kaufman, R. P., Jr., Ross, J. S., The prognostic significance of p34cdc2 and cyclin D1 protein expression in prostate adenocarcinoma, *Cancer* 1997; 80; 753-763. Mann-Whitney test, Pearson Chi-square test and chi-square test were appropriately applied for analysis of continuous and categorical variables respectively. All tests were two-sided and p value of 0.05 was considered as significant.

Analysis of 80 Patients with Prostate Cancer and 28 with Metastatic Lesions

The median age of patients in the primary prostate cancer group was 62 years (range 40 to 89 years). The commonest site of the primary prostate cancer was recorded as multi-quadrant followed by involvement of left and right posterior lobes. The median cancer dimension was 1.65 cm (range 0.1 to 4.8 cm). The pre-operative PSA level ranged from 0-312 (median 6.25). Of these 80 cases, 19 (23.8%) were low grade (Gleason's score .ltoreq.6) and 61(76.2%) had a Gleason score greater than 6. When the cases were enumerated by pattern, the distribution is as shown in Table 1. The metastatic sites included lymph nodes (17), bone including skull and spine (9) and bladder (2).

Nuclear expression of AR was noted in primary as well as metastatic tumor tissues. The mean AR expression in the primary tumor was greater than that in normal glands and the difference was statistically significant (p=0.02). Nuclear AR expression was observed in all primary tumors; its expression did not correlate with any of the variables analyzed. There was no significant difference in the AR expression between primary and metastatic tumors (p=0.44).

GATA3 expression was completely negative in normal as well as primary and metastatic prostatic tumor tissues.

Nuclear expression of FOXA1 was noted in normal prostatic glands (72/80), as well as in all primary and metastatic tumors. The $75^{th}$ percentile of FOXA1 expression score in tumor cells (≤200) was taken as a cut-off value and the score was divided in two groups: $FOXA1_{low}$ (<200) and $FOXA1_{high}$ (>200). Amongst the 72 normal prostatic glands showing FOXA1 expression, high level expression was seen in 31 cases (43%) and low level in 41 cases (57%). The mean FOXA1 expression in the primary tumor was lower than in normal tissue although not statistically significant (p=0.17). Low FOXA1 staining was observed in 65 cases (81%) and high in 15 cases (19%) of primary cancer. FOXA1 did not correlate with histological pattern or with combined Gleason score (tables 1 and 2).

TABLE 1

Correlation of FOXA1 expression with Gleason Pattern.

| Pattern | Number | $FOXA1_{low}$ | $FOX1_{high}$ | P value |
|---|---|---|---|---|
| 3 | 73 | 62 (84.9) | 11 (15.1) | 0.65$ |
| 4 | 58 | 48 (82.8) | 10 (17.2) | |
| 5 | 31 | 24 (77.4) | 7 (22.6) | |

$Chi-square test

TABLE 2

Comparison of FOXA1 score with clinic-pathologic variables

| Variables | FOXA1 low | FOXA1 high | P value |
|---|---|---|---|
| Age (Median, Range) | 62 (40-89) | 64 (52-83) | 0.38† |
| Cancer dimension (Median, Range) | 1.6 (0.1-4.8) | 2.2 (1.3-4.0) | 0.05† |
| PSA (Median, Range) | 6.0 (0-312) | 9.7 (3.3-3.0) | 0.20† |
| Grade (category) | | | |
| ≤6 | 17 (26.1) | 3 (20) | 0.50‡ |
| >6 | 48 (73.9) | 12 (80) | |
| Multifocality | | | |
| No | 3 (6.1) | 0 (0) | 1‡ |
| Yes | 46 (93.9) | 14 (100) | |
| Extraprostatic Extension | | | |
| No | 32 (54.2) | 3 (20.0) | 0.02‡ |
| Yes | 27 (45.8) | 12 (80.0) | |
| Seminal Vesicle Invasion | | | |
| No | 50 (82.0) | 10 (66.7) | 0.29‡ |
| Yes | 11 (18.0) | 5 (33.3) | |
| PIN | | | |

TABLE 2-continued

Comparison of FOXA1 score with clinic-pathologic variables

| Variables | FOXA1 low | FOXA1 high | P value |
|---|---|---|---|
| No | 2 (4.4) | 1 (7.7) | |
| Yes | 43 (95.6) | 12 (92.3) | 0.54‡ |
| Angiolymphatic Invasion | | | |
| No | 45 (79.0) | 8 (53.3) | 0.05‡ |
| Yes | 12 (21.0) | 7 (46.7) | |
| Perineural invasion | | | |
| No | 8 (12.7) | 1 (6.7) | 1‡ |
| Yes | 55 (87.3) | 14 (93.3) | |
| T Stage | | | |
| T2 | 2 (40.0) | 31 (55.4) | 0.13‡ |
| T3 | 3 (60.0) | 25 (44.6) | |
| Surgical Margins | | | |
| No | 38 (60.3) | 9 (60.0) | 1‡ |
| Yes | 25 (39.7) | 6 (40.0) | |
| Metastasis | | | |
| No | 57 (87.6) | 8 (53.3) | 0.0068‡ |
| Yes | 8 (12.4) | 7 (47.7) | |

†Mann Whitney Test;
‡Pearson Chi square test;
PSA - Prostate specific antigen;
PIN - Prostate intraepithelial neoplasia Similarly, age, multifocality, seminal vesicle invasion, perineural invasion, surgical margin status and T stage did not correlate with FOXA1 status (Table 2). High FOXA1 expression significantly correlated with tumor size, angiolympatic invasion and extra prostatic extension and AR (p=0.05, 0.05, 0.02 and 0.001 respectively). Forty seven percent (7/15) of primary cancer with high FOXA1 score developed metastasis and 88% with low FOXA1 score did not metastasize (p=0.0068). Information on nodal status was available for 46 primary tumor cases of which 16 (35%) were nodal positive.

Twenty-five of the 28 metastatic cases (89%) showed high FOXA1 expression. In the matched series of 15 cases, 7 of the primary tumors and all 15 metastatic cases showed high FOXA1 expression. A statistically significant difference was observed between FOXA1 expression in primary and metastatic prostate cancers (p<0.0001).

Validation of the Relationship Between Elevated Levels of FOXA1 and Metatastic Prostate Cancer.

TMA Description

Expression of FOXA1 was analyzed in a tissue microarray of 117 prostate cancer patients from Seoul, Korea selected from 2000-2003 using immunohistochemistry. Ten tissue microarrays (TMAs) were prepared using 0.6µ triplicate cores from these patients along with one core from corresponding normal tissue adjacent to the tumor foci.

IHC Analysis

Expression of FOXA1 was analyzed by immunohistochemistry using goat anti-FOXA1 antibody (SantaCruz Lab) using antigen retrieval and reactivity was visualized using Envision kit (DAKO Cytomation) using previously described methods (see Badve, S., et al., Clin Cancer Res 2007; 13; 4415-4421). All TMAs were stained for FOXA1 and the nuclear expression was noted in primary tumor as well as in normal prostatic tissues Expression of FOXA1/ was recorded both as intensity and percentage. Percentage ranged from 0 to 100 and intensity was graded as none (0), mild (1+), moderate (2+) and strong (3+). Percentage (P) and intensity (I) of nuclear expression were multiplied to generate a numerical expression score (S=P×I) ranging from 0 to 300. Statistical analyses were performed using SPSS 17.0. FOXA1 expressions were correlated with the clinic-pathological variables recorded using Spearman correlation test. Gleason grade was analyzed both as individual pattern as well as combined score (high grade (>6) and low grade (≤6)). Mann-Whitney test, Pearson Chi-square test and chi-square test were appropriately applied for analysis of continuous and categorical variables respectively. All tests were two-sided and p value of 0.05 was considered as significant.

Figure 3A:
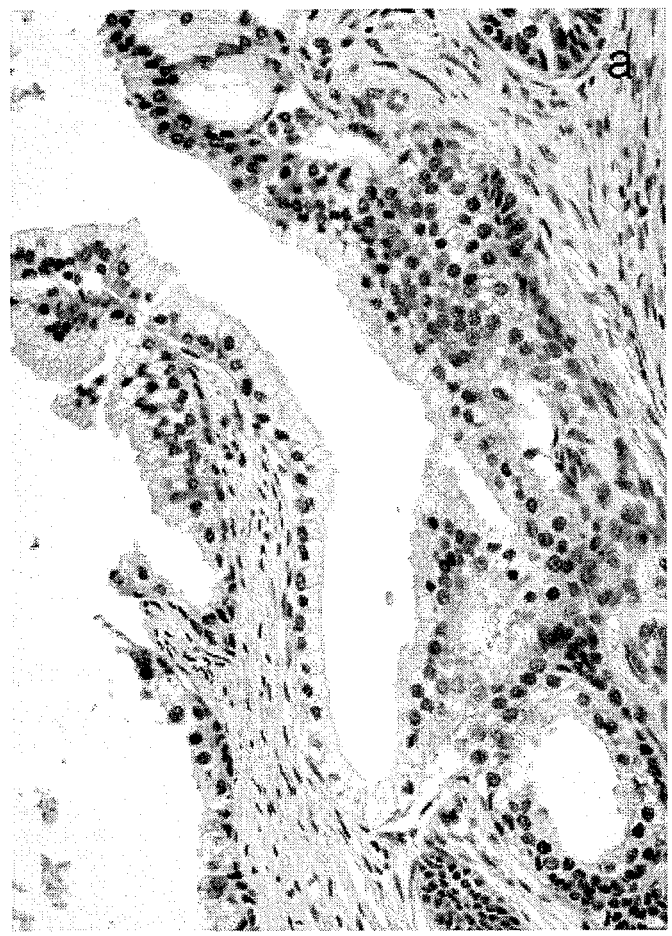
FIG. 3A. Photomicrograph showing the expression level of FOXA1 in normal prostate tissue determined by immunohistochemical staining.
Figure 3B:
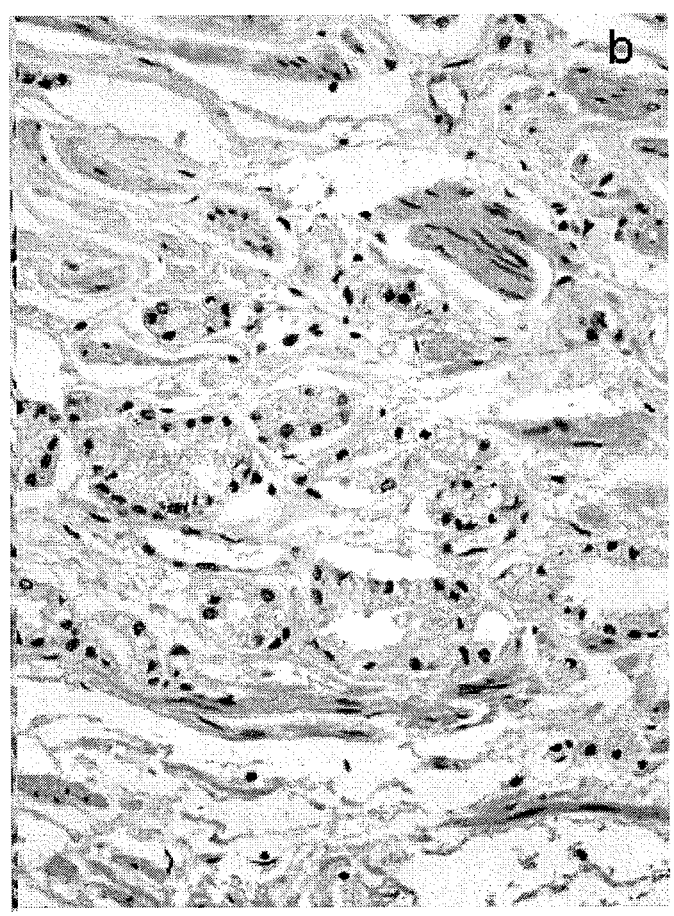
FIG. 3B. Photomicrograph showing the expression level of F FOXA1 in prostate cancer tissue determined by immunohistochemical staining.
Figure 3C:
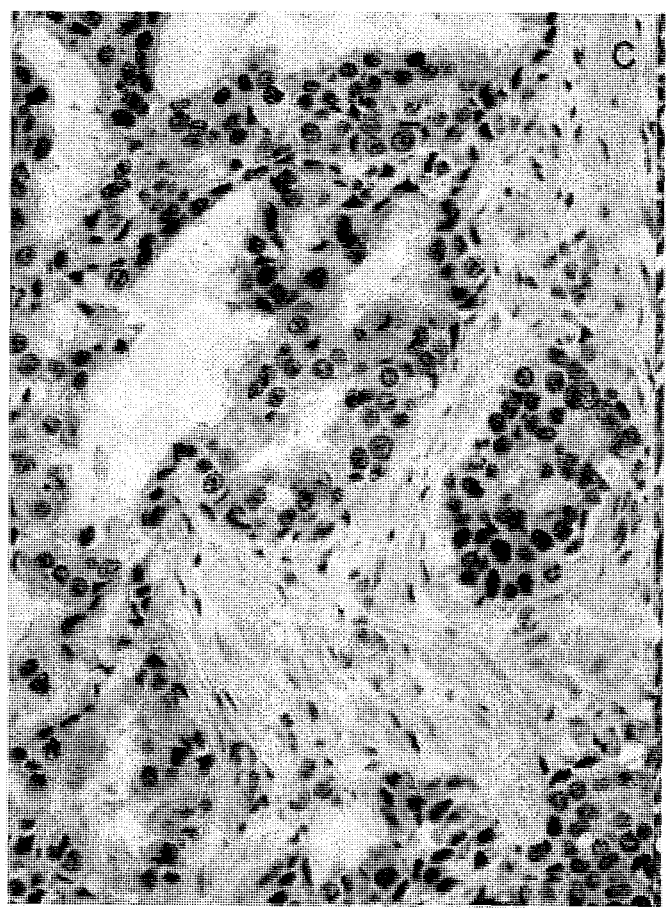
FIG. 3C. Photomicrograph showing the expression level of F FOXA1 in prostate cancer tissue synchronous metastasis.
Figure 3D:
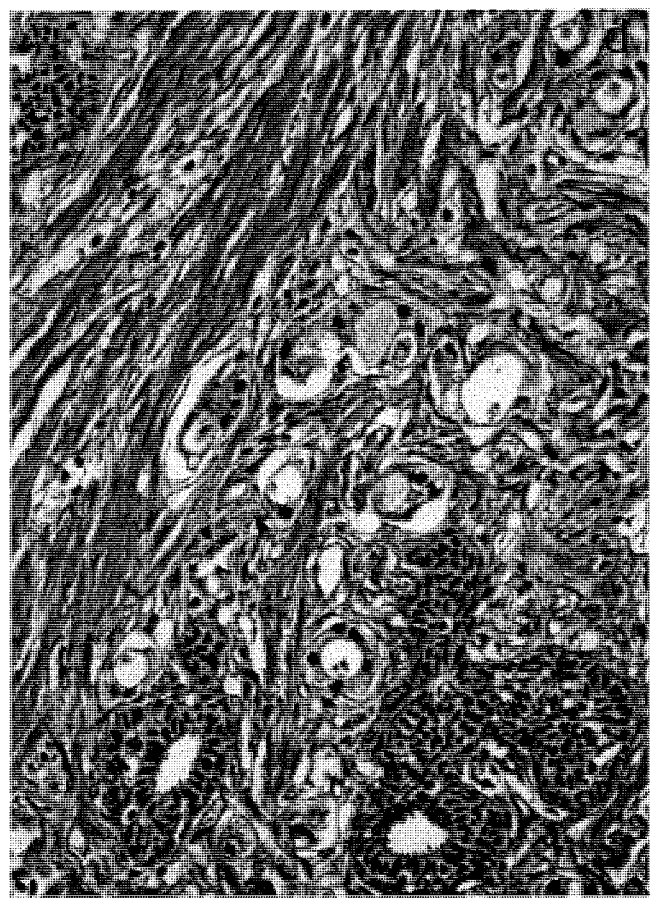
FIG. 3D. Photomicrograph showing the expression level of F FOXA1 in prostate cancer tissue metachronous metastasis.

Referring now to FIGS. 3A-D Immunohistochemical expression of FOXA1 in normal prostate (a) and prostate cancer (b-d). Note the high expression in primary tumors (c and d), with synchronous or metachronous metastases, respectively (For IHC details, please refer to Badve, et al., Clin Can Res, 2007 and Ademuyiwa et al. Mod Path, 2010).

A total of 117 cases were evaluated for expression of FOXA1. Each of the three tumor cores from every case was scored separately and the average of these was used for analyses. The mean age of patients in this cohort was 64.04±6.6. The average tumor size was 2.6±1.1 and the average PSA level was 13.8±10.8. The mean Gleason score was 7.08±1.2. Of these 117 patients 20 patients developed metastasis that included cases with nodal and/or distant metastases at surgery or metachronously after surgery in places like lung and bone.

Nuclear expression of FOXA1 was noted in normal prostatic glands, as well as in primary tumors. Out of 117 cases FOXA1 expression was scored in 111 cases while in 6 cases there was loss of tumor tissue. The median of the average tumor FOXA1 score (140) was taken as a cut-off value and the score was divided in two groups: $FOXA1_{low}$ (≤140) and $FOXA1_{high}$ (>140). Low FOXA1 staining was observed in 56 (47.9%) cases and high in 61 cases (52.1%).

The mean FOXA1 expression in normal prostatic tissue was significantly lower than in the corresponding tumor tissue (p<0.0001). High FOXA1 expression in primary prostate tumors correlated positively with positive metastatic status that included cases with nodal and/or distant metastases at surgery or metachronously after surgery (p=0.006). It also positively correlated with extra-prostatic extension (p=0.037), seminal vesicle invasion (p=0.048), perineural invasion (p=0.008) and T stage (p=0.023). It did not correlate with age, PSA level at diagnosis, Surgical margins, Gleason score (categorized as well as continuous) and angiolymphatic invasion.

TABLE 3

Comparison of FOXA1 score with clinic-pathologic variables.

| Variables | FOXA1 low | FOXA1 high | P value |
|---|---|---|---|
| Age (Median, Range) | 65 (45-76) | 63 (48-79) | NS |
| Cancer dimension (Median, Range) | 2.5 (0.6-5.0) | 2.5 (0.9-5.5) | NS |
| PSA (Median, Range) | | | |
| Grade (category) | 9.5 (2-42) | 10.10 (0-53) | NS |
| ≤6 | 12 (21.4) | 6 (10.9) | |
| >6 | 44 (78.6) | 49 (89.1) | NS |
| Extraprostatic extension | | | |
| No | 35 (62.5) | 23 (41.8) | |
| Yes | 21 (37.5) | 32 (58.2) | 0.037 |
| Seminal vesicle invasion | | | |

TABLE 3-continued

Comparison of FOXA1 score with clinic-pathologic variables.

| Variables | FOXA1 low | FOXA1 high | P value |
|---|---|---|---|
| No | 47 (83.9) | 37 (67.3) | |
| Yes | 9 (16.1) | 18 (32.7) | 0.048 |
| Angiolymphatic invasion | | | |
| No | 45 (80.4) | 41 (74.5) | |
| Yes | 11 (19.6) | 14 (25.5) | NS |
| Perineural invasion | | | |
| No | 17 (30.4) | 5 (9.1) | |
| Yes | 39 (69.6) | 50 (90.9) | 0.008 |
| T Stage | | | |
| T2 | 35 (62.5) | 22 (40.0) | |
| T3 | 21 (37.5 | 33 (60.0) | 0.023 |
| Surgical Margins | | | |
| No | 27 (48.2) | 22 (40.0) | |
| Yes | 29 (51.8) | 33 (60.0) | NS |
| Metastasis | | | |
| No | 52 (92.9) | 40 (72.7) | |
| Yes | 4 (7.1) | 15 (27.3) | 0.006 |

As illustrated by the results disclosed herein, high FOXA1 expression predicts for greater likelihood for development of metastasis. This validation study serves to confirm that FOXA1 expression could be used to identify cancers with a propensity to metastasize fulfilling an unmet need for a predictor of biologic behaviour of prostate cancer. This also raises the strong possibility that the expression of downstream molecules of FOXA1 could be used as a predictive marker in prostate cancer. In addition, modulating FOXA1 expression in prostate cancer may be a potential therapeutic approach. Further, validation in larger datasets with adequate follow-up is warranted.

While the novel technology has been illustrated and described in detail in the figures and foregoing description, the same is to be considered as illustrative and not restrictive in character; it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of treating a patient having prostate cancer, the method comprising:
   identifying the patient as having prostate cancer by detecting an increased expression level of Forkhead-box A1 (FOXA1) in a sample obtained from the patient, wherein the FOXA1 expression level identifies the patient as having prostate cancer; and
   treating the patient with at least one compound or a pharmaceutically acceptable salt thereof selected from the group consisting of paclitaxel, docetaxel, cisplatin, methotrexate, cyclophosphamide, 5-fluoro uridine, leucovorin, irinotecan, carboplatin, doxorubicin, fluorouracil carboplatin, edatrexate, gemcitabine, vinorelbine and combinations thereof by administering the at least one compound or the pharmaceutically acceptable salt thereof to the patient.

2. The method of claim 1, wherein the FOXA1 is FOXA1 protein.

3. The method of claim 2, wherein the probe is an antibody.

4. The method of claim 1, wherein the FOXA1 is FOXA1 gene.

5. The method of claim 4, wherein the probe is a nucleic acid.

6. A method of treating a patient identified as having metastatic prostate cancer, the method comprising:
   identifying the patient as having metastatic prostate cancer by detecting an increased expression level of Forkhead-box A1 (FOXA1) in a sample obtained from the patient, wherein the FOXA1 expression level having a numerical expression score greater than 275 identifies the patient as having metastatic prostate cancer; and
   treating the patient with at least one compound or a pharmaceutically acceptable salt thereof selected from the group consisting of paclitaxel, docetaxel, cisplatin, methotrexate, cyclophosphamide, 5-fluoro uridine, leucovorin, irinotecan, carboplatin, doxorubicin, fluorouracil carboplatin, edatrexate, gemcitabine, vinorelbine and combinations thereof by administering the at least one compound or the pharmaceutically acceptable salt thereof to the patient.

7. The method of claim 6, wherein the FOXA1 is FOXA1 protein.

8. The method of claim 7, wherein the probe is an antibody.

9. The method of claim 6, wherein the FOXA1 is FOXA1 gene.

10. The method of claim 9, wherein the probe is a nucleic acid.

11. The method of claim 6, wherein the numerical expression score is greater than 280.

* * * * *

SEQUENCE LISTING

```
<160> NUMBER OF SEQ ID NOS: 1

<210> SEQ ID NO 1
<211> LENGTH: 1419
<212> TYPE: DNA
<213> ORGANISM: Homo sapiens

<400> SEQUENCE: 1
atgttaggaa ctgtgaagat ggaagggcat gaaaccagcg actggaacag ctactacgca      60
gacacgcagg aggcctactc ctccgtcccg gtcagcaaca tgaactcagg cctgggctcc     120
atgaactcca tgaacaccta catgaccatg aacaccatga ctacgagcgg caacatgacc     180
ccggcgtcct tcaacatgtc ctatgccaac ccgggcctag gggccggcct gagtcccggc     240
gcagtagccg gcatgccggg gggctcggcg ggcgccatga acagcatgac tgcggccggc     300
gtgacggcca tgggtacggc gctgagcccg agcggcatgg gcgccatggg tgcgcagcag     360
gcggcctcca tgaatggcct gggcccctac gcggccgcca tgaacccgtg catgagcccc     420
atggcgtacg cgccgtccaa cctgggccgc agccgcgcgg gcggcggcgg cgacgccaag     480
acgttcaagc gcagctaccc gcacgccaag ccgccctact cgtacatctc gctcatcacc     540
atggccatcc agcaggcgcc cagcaagatg ctcacgctga gcgagatcta ccagtggatc     600
atggacctct tccctatta ccggcagaac cagcagcgct ggcagaactc catccgccac     660
tcgctgtcct tcaatgactg cttcgtcaag gtggcacgct ccccggacaa gccgggcaag     720
ggctcctact ggacgctgca cccggactcc ggcaacatgt tcgagaacgg ctgctacttg     780
cgccgccaga gcgcttcaa gtgcgagaag cagccggggg ccggcggcgg gggcgggagc     840
ggaagcgggg gcagcggcgc caagggcggc cctgagagcc gcaaggaccc ctctggcgcc     900
tctaacccca gcgccgactc gccccctccat cggggtgtgc acgggaagac cggccagcta     960
gagggcgcgc cggccccgg gcccgccgcc agcccccaga ctctggacca cagtggggcg    1020
```

```
acggcgacag ggggcgcctc ggagttgaag actccagcct cctcaactgc gcccccata    1080 agctccgggc ccggggcgct ggcctctgtg cccgcctctc acccggcaca cggcttggca    1140
ccccacgagt cccagctgca cctgaaaggg gaccccact actccttcaa ccacccgttc     1200
tccatcaaca acctcatgtc ctcctcggag cagcagcata agctggactt caaggcatac    1260
gaacaggcac tgcaatactc gccttacggc tctacgttgc ccgccagcct gcctctaggc    1320
agcgcctcgg tgaccaccag gagccccatc gagccctcag ccctggagcc ggcgtactac    1380
caaggtgtgt attccagacc cgtcctaaac acttcctag                            1419
```